(12) United States Patent
Ellman

(10) Patent No.: US 9,113,854 B2
(45) Date of Patent: Aug. 25, 2015

(54) TISSUE RETRACTOR

(71) Applicant: Alan G Ellman, Hewlett, NY (US)

(72) Inventor: Alan G Ellman, Hewlett, NY (US)

( * ) Notice: Subject to any disclaimer, the term of this patent is extended or adjusted under 35 U.S.C. 154(b) by 255 days.

(21) Appl. No.: 13/657,516

(22) Filed: Oct. 22, 2012

(65) Prior Publication Data

US 2014/0114140 A1    Apr. 24, 2014

(51) Int. Cl.
*A61B 1/32* (2006.01)
*A61B 17/02* (2006.01)

(52) U.S. Cl.
CPC ........... *A61B 17/0218* (2013.01); *A61B 17/025* (2013.01); *A61B 17/0206* (2013.01); *A61B 2017/0256* (2013.01)

(58) Field of Classification Search
CPC .......................... A61B 17/0293; A61B 17/0206
USPC ................... 600/214, 219, 221, 222, 224, 225
See application file for complete search history.

(56) References Cited

U.S. PATENT DOCUMENTS

| | | | |
|---|---|---|---|
| 380,745 A * | 4/1888 | Chamberlin | 600/224 |
| 3,729,006 A | 4/1973 | Wilder et al. | |
| 6,280,379 B1 | 8/2001 | Resnick | |
| 7,374,534 B2 | 5/2008 | Dalton | |
| 2006/0106416 A1 | 5/2006 | Raymond | |
| 2007/0073112 A1 * | 3/2007 | Holmes | 600/225 |
| 2007/0293729 A1 | 12/2007 | Grey et al. | |
| 2008/0058606 A1 * | 3/2008 | Miles et al. | 600/214 |
| 2008/0132764 A1 | 6/2008 | Hamada | |
| 2013/0066154 A1 * | 3/2013 | Mangiardi | 600/202 |

OTHER PUBLICATIONS

Office Action in U.S. Appl. No. 13/899,492.
Office Action in U.S. Appl. No. 13/900,486.

* cited by examiner

*Primary Examiner* — Nicholas Woodall
*Assistant Examiner* — Olivia C Chang

(57) ABSTRACT

A tissue retractor device suitable for spinal surgery. The device includes base apparatus to which three blades are circumferentially hinged, the blades closing upon each other in default position from spring bias. A pusher mechanism is threadably connected to the base which spreads the blades by rotating the pusher in its threads relative to the base, which converts rotational motion to translational motion to angular motion of the blades about their respective hinges. One blade is longer than the others to present a multipurpose tip to the user of the device, such a tip being useful in avoiding nerve roots or other anatomy obstructing the surgical path. A dilator is threadably connected to the pusher, the dilator having a long hollow tube connected to a hollow tip extending beyond the blades to slide over guide-wire and initially position the device at the operative site, prior to using the pusher to retract patient's tissue.

12 Claims, 8 Drawing Sheets

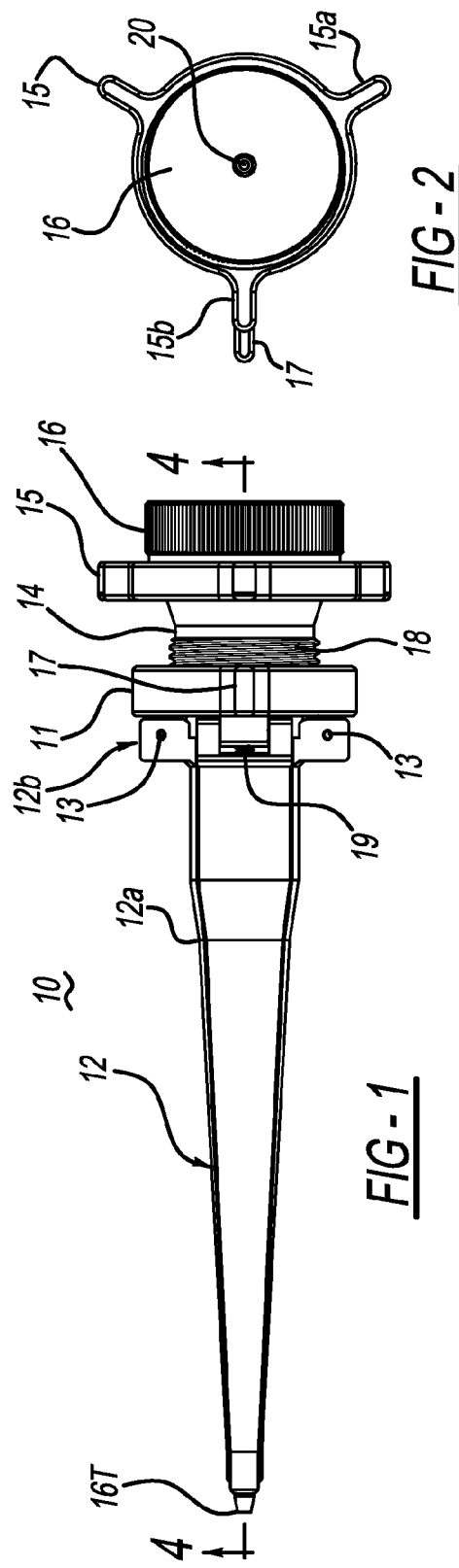
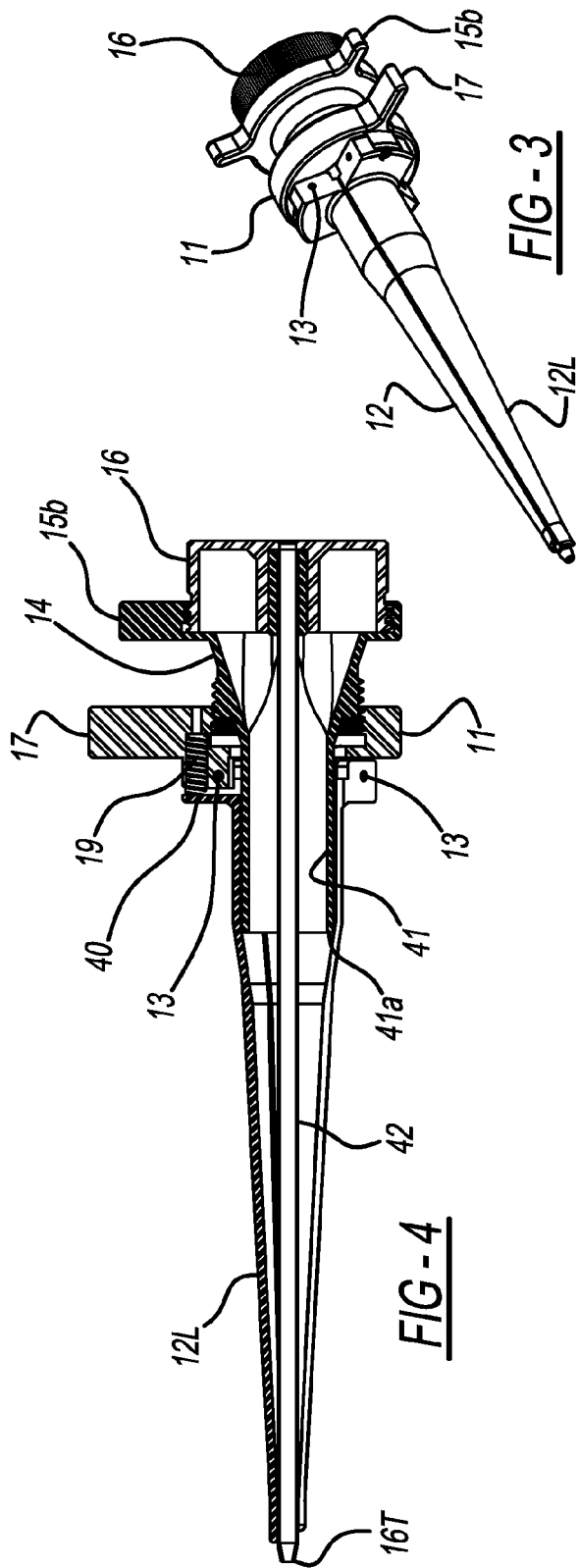

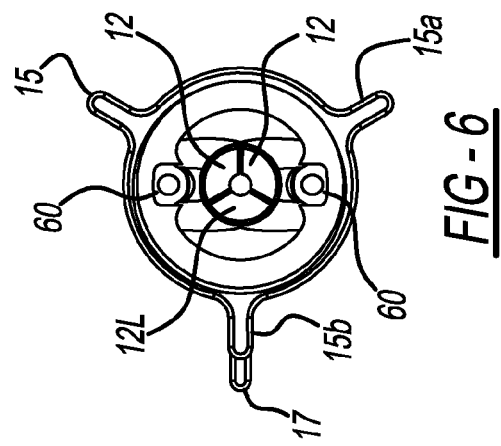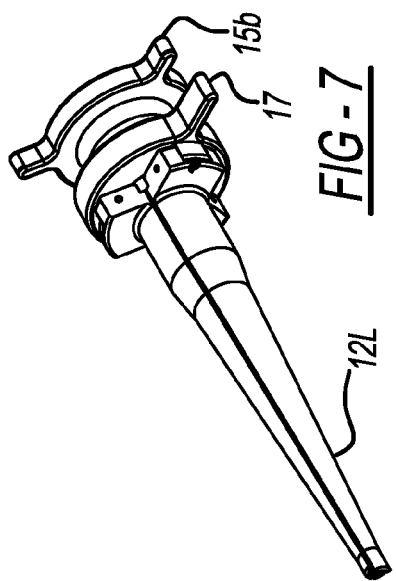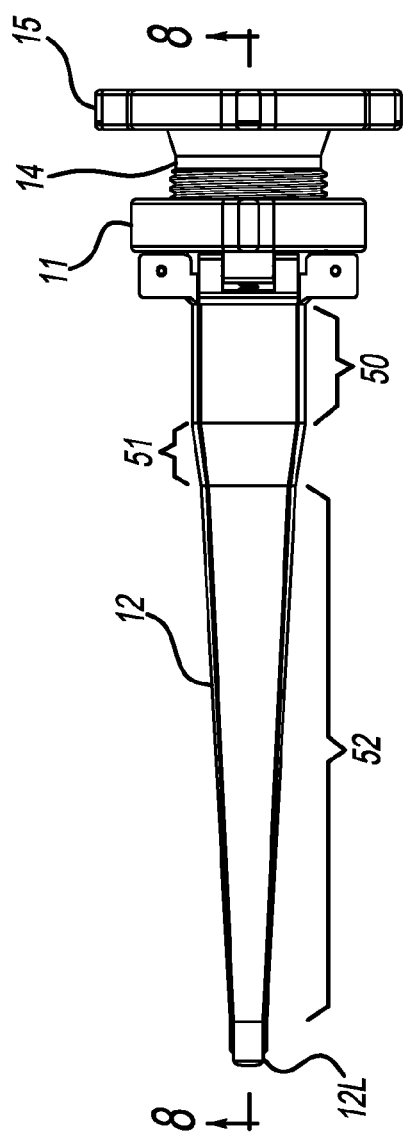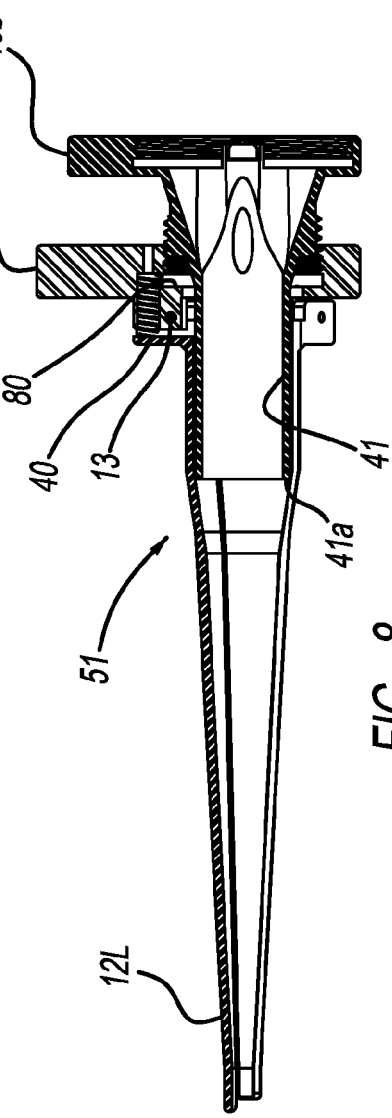

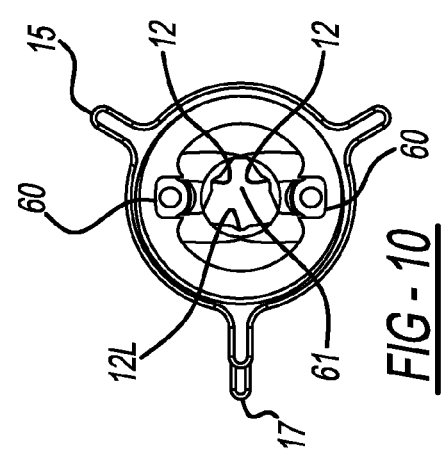
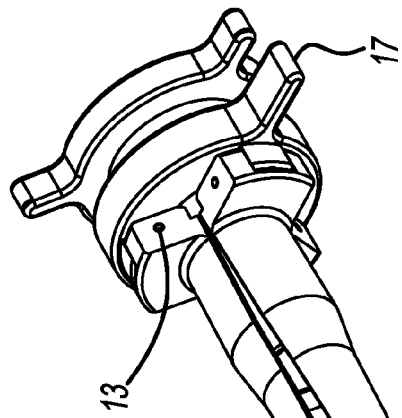
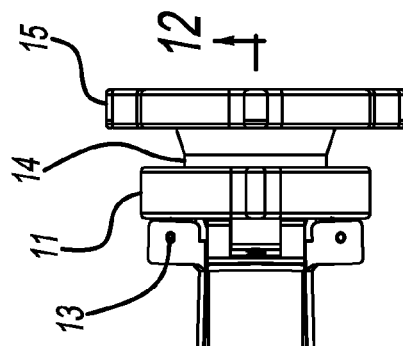
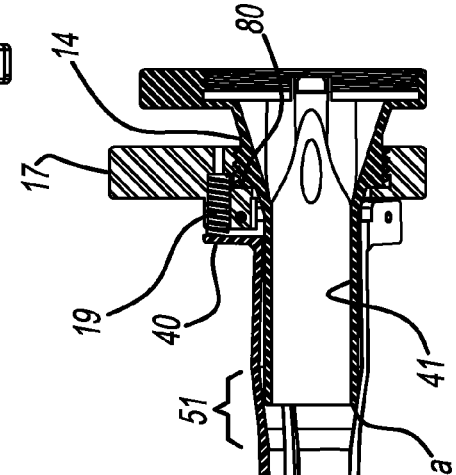
FIG-10
FIG-11
FIG-9
FIG-12

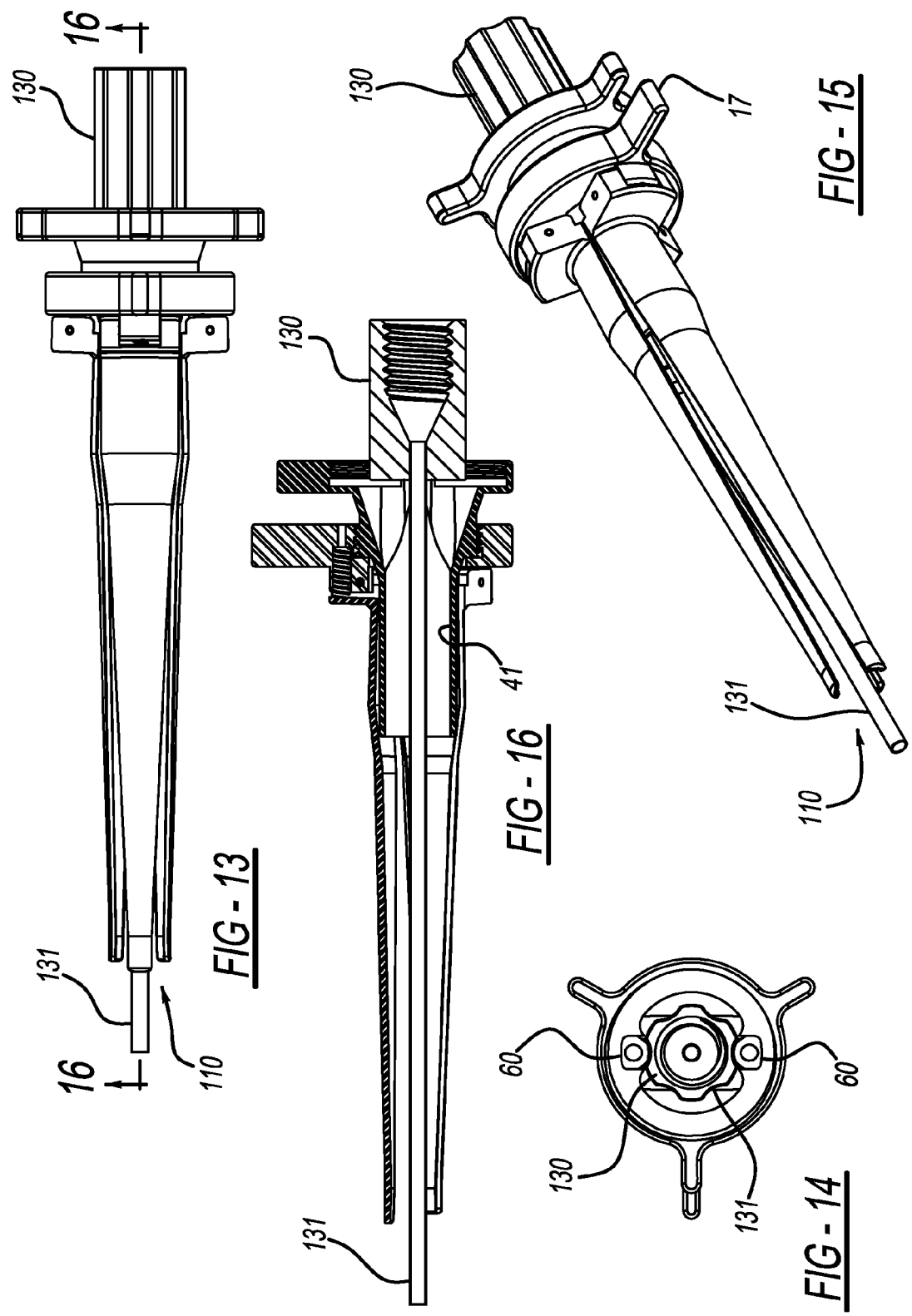

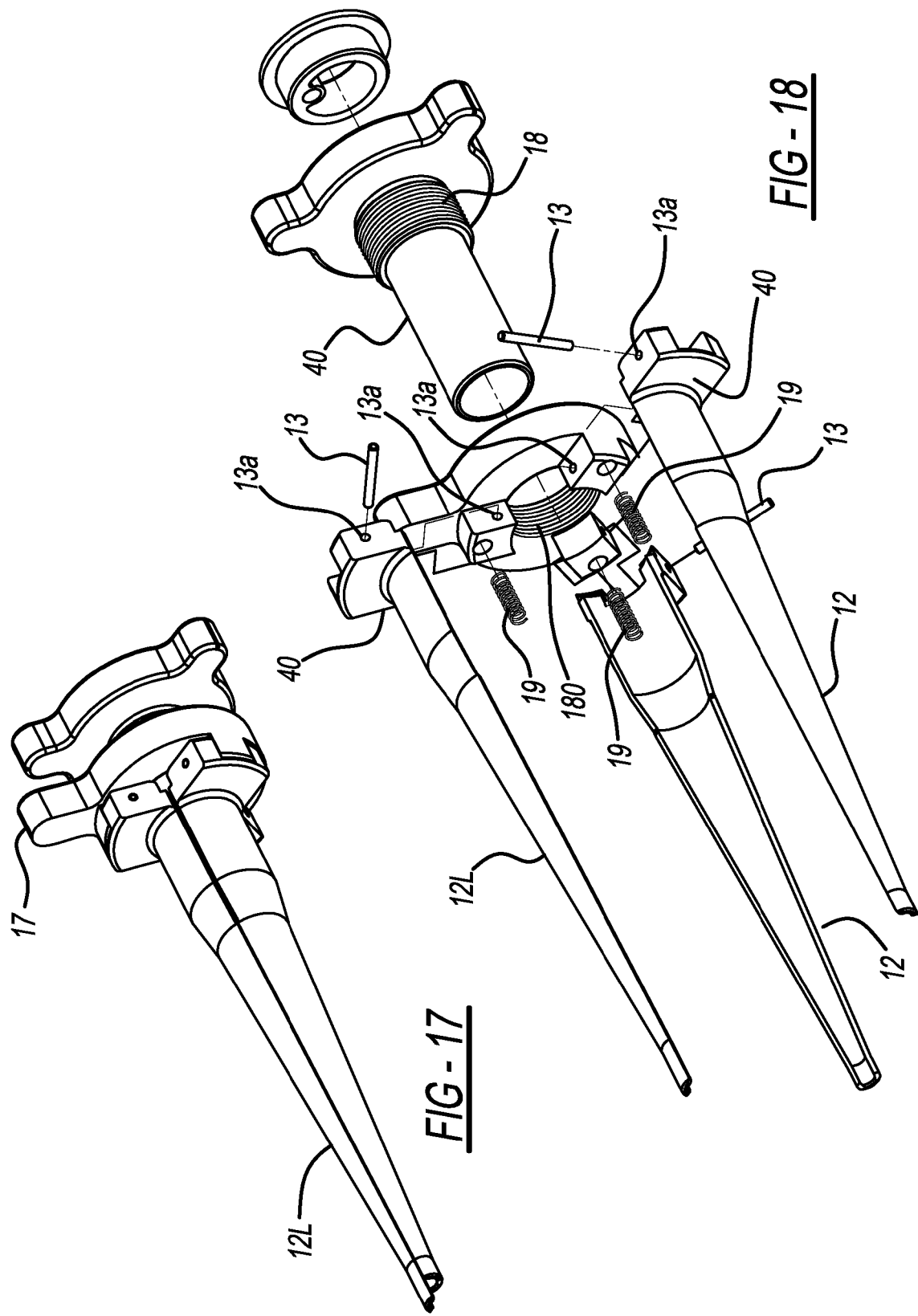

to Dalton, which is incorporated herein by reference in its entirety. The present invention provides an improved retractor device which improves chances of avoiding undesired results and thereby greatly improves chances of achieving a successful patient outcome. Furthermore, the present invention provides greater control, precision, ease of use and may have utility in surgical procedures performed in operative fields other than those discussed herein. Other advantages and features will become apparent from the description of the invention.

TISSUE RETRACTOR

BACKGROUND

The present invention relates to a device and method for expanding an enclosure such as tissue to expose the operative field in a patient. Entering an operative field such as in connection with specialized back surgery on or in-between vertebrae of the spine and on spinal discs involves various meticulous surgical procedures which can be challenging even for experienced surgeons who specialize in this particular surgery. Minimally invasive techniques are preferred over traditional open surgical procedures which require extensive operating time and post-operative recovery time.

When employing such minimally invasive surgical techniques, one of the challenging requirements relates to safe retraction of patient tissue in the target area or operative field to provide sufficient space for implementation of these techniques. For example, nerve roots are plentiful in this operative field and extreme care must be exercised by the surgeon to avoid accidentally damaging or even severing any of these roots when retracting tissue in this operative field. An example of a tissue retractor which does not include improvements, advancements and advantages of the present invention is provided in U.S. Pat. No. 7,374,534 issued on May 20, 2008 to Dalton, which is incorporated herein by reference in its entirety. The present invention provides an improved retractor device which improves chances of avoiding undesired results and thereby greatly improves chances of achieving a successful patient outcome. Furthermore, the present invention provides greater control, precision, ease of use and may have utility in surgical procedures performed in operative fields other than those discussed herein. Other advantages and features will become apparent from the description of the invention.

SUMMARY

In summary, an embodiment of relates to a tissue retractor device and/or to a method for performing a surgical procedure using that device on a patient by a surgeon. The device includes a base hinged to a number of blades circumferentially distributed around the base. In one embodiment, each of the blades is spring-biased so that the blades close upon themselves in the default state. Each of the blades is rotatable relative to its respective hinge when utilizing the retractor device under the control of the surgeon. In one embodiment, one of the blades is longer than all of the other blades, thereby providing an advantageously-smaller device-tip configuration by which the surgeon can better control such longer blade to maneuver around, and between, nerve roots and other critical elements lying in its path after the device has been surgically inserted into the patient.

In one aspect, the device further includes a pusher mechanism which is threadably and concentrically connected within the base. Again, after the device has been surgically inserted into the patient, the pusher interacts with the blades in a manner to controllably and angularly displace each of the blades from its respective closed position about its respective hinge, responsive to the surgeon's manually-rotating the pusher in the threaded connection relative to the base.

To facilitate the surgical insertion or implantation of the device, the device further includes a dilator mechanism thread-ably and concentrically connected within the pusher. The dilator, in one embodiment, includes a concentrically located shaft having a tip at the end of the shaft which protrudes beyond the end of the largest one blade. The dilator tip is suitable for penetrating or pushing into the body of the patient while each of the blades is in its respective closed position and before the surgeon operates the pusher to displace the blades. And, the tip is particularly suitable for maneuvering between adjacent vertebrae in the spine of the patient if back surgery is being performed. However, it will be understood that the present embodiment may be used in broader surgical procedures beyond spinal surgery including OB/GYN, or even non-surgical procedures where one desires to expand a particular area.

In another embodiment, a method relates to first inserting a guide-wire into the spinal area of a patient to a desired depth. Then the above-described tissue retracting device including the dilator having a tip protruding beyond any other structure of that device is slid over the guide-wire. The device is inserted into the patient to a desired depth, the surgeon maneuvering the tip between target vertebrae, the maneuvering including clockwise and counter clockwise rotation of the device while the blades remain closed. Under certain circumstances, the guide-wire may be removed from the patient, either prior to, concurrently with, or subsequent to the dilator tip maneuvering. However, if the guide-wire was not previously removed, after the dilator tip is properly positioned (wherefore ends of the blades are properly positioned), the dilator and the guide-wire are both removed together from the device, leaving an inserted portion of the remainder of the device including at least a portion of its blades in the patient. The non-inserted portion includes the accessible circularly-shaped base noted above, hinged to the inserted blades, where one of the blades is longer than the other two equally-sized blades. The surgeon maneuvers the one blade beyond and around nerve roots that are in the vicinity of the target vertebrae, thereby safely clearing a pathway between and amongst those nerve roots which otherwise obstruct the surgeon's performance. The surgeon then operates the pusher mechanism by rotating its knob relative to the base and controllably displaces each of the blades from its respective closed position to cause tissue of the patient's body to be retracted. This provides space at the location of the operative field for surgical activity. Finally, the surgeon inserts a surgical tool, perhaps inserting one of several tools in sequence, into the device when the device's blades are displaced, and uses each such tool to perform the necessary surgery.

BRIEF DESCRIPTION OF THE DRAWINGS

FIG. 1 is a top plan view of an exemplary embodiment of a retractor device including its dilator, configured for insertion into a patient;

FIG. 2 is an end view of the configuration of FIG. 1;

FIG. 3 is a perspective view of the embodiment of FIG. 1;

FIG. 4 is a cross-sectional view of the embodiment of FIG. 1, sliced by vertical plane 4-4;

FIG. 5 is a top plan view of the exemplary embodiment of FIG. 1 after the dilator has been removed;

FIG. 6 is an end view of the configuration of FIG. 5, being the same end view as that of FIG. 2 but with the dilator removed;

FIG. 7 is the same perspective view as that presented in FIG. 3, but with the dilator removed;

FIG. 8 is a cross-sectional view of the embodiment of FIG. 5, sliced by vertical plane 8-8;

FIG. 9 is a top plan view of the exemplary embodiment of FIG. 5, after the blades have been outwardly displaced or spread apart;

FIG. 10 is an end view of the configuration of FIG. 9, being the same end view as that of FIG. 6 but with the blades spread apart;

FIG. 11 is the same perspective view as that presented in FIG. 7, but with the blades outwardly displaced;

FIG. 12 is a cross-sectional view of the embodiment of FIG. 9, sliced by the vertical plane 12-12;

FIG. 13 is a top plan view of the exemplary embodiment of FIG. 9, but after a surgical tool had been inserted into the embodiment;

FIG. 14 is an end view of the configuration of FIG. 13, being the same end view as that of FIG. 10 but with the surgical tool in place;

FIG. 15 is the same perspective view as that presented in FIG. 11, but with the surgical tool in place;

FIG. 16 is a cross-sectional view of the embodiment of FIG. 13, sliced by the vertical plane 16-16;

FIG. 17 is another perspective view, similar to, but axially rotated from, that of FIG. 7, to more clearly show that one blade is longer than the other blades, and more clearly show the base finger-tab or handle permanently aligned with the longer blade;

FIG. 18 is an exploded view of the embodiment of FIG. 17, but axially rotated therefrom to more clearly show certain detailed mechanical features of the embodiment;

DETAILED DESCRIPTION OF PREFERRED EMBODIMENTS

Figure 19:
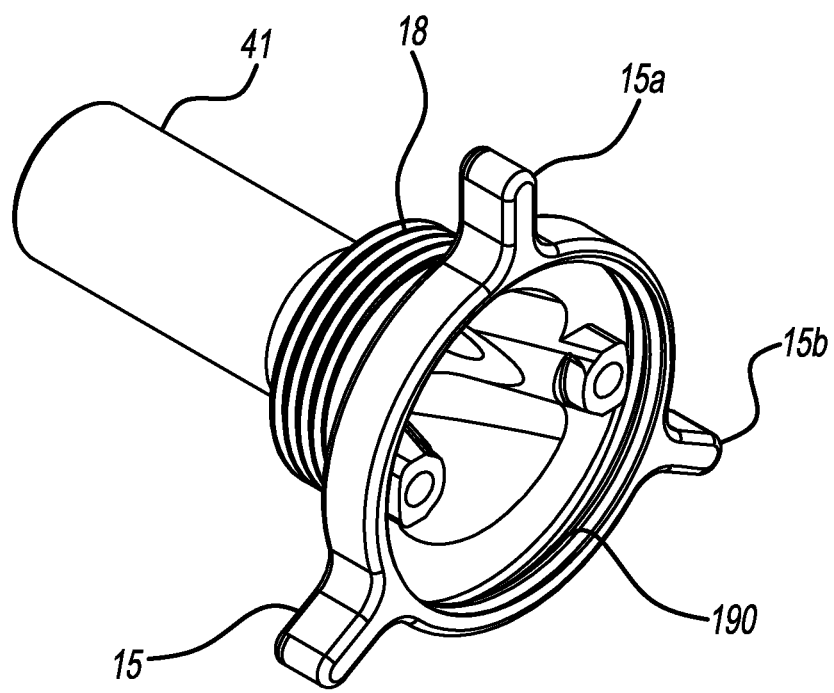
FIG. 19 is a perspective view of the pusher mechanism shown in cross section in FIGS. 4, 8, 12 and 16.

In this description, the same reference numeral in different Figs. refers to the same entity. Otherwise, reference numerals of each FIG. start with the same number as the number of that FIG. For example, FIG. 3 has numerals in the "30" category and FIG. 4 has numerals in the "40" category, etc.

FIG. 1 is a top plan view of tissue retractor device 10 according to one embodiment of the present invention. Retractor device 10 may be constructed from stainless steel and/or hard or elastic or plastic and/or other materials suitable for use as, or within, a surgically invasive tool for use in surgical procedures upon a human body. Alternatively, retractor 10 may be constructed from a material that is compatible with a visualization system, e.g., a fluoroscope or a magnetic resonance imaging (MRI) machine, where the tip of its longest blade (discussed below) is radio opaque to allow the user to visualize, in real time as the surgery is progressing, exactly where the end of that device blade is located in the body of the patient.

Base 11 can be a circular structure and includes screw-threads formed therein (threads 180 in FIG. 18) for thread-ably engaging threads 18 which are formed on the outside of pusher mechanism 14. (Base 11 includes certain structure which is analogous to a nut having threads formed therein which can receive threads of a compatibly-mated bolt, the latter being analogous to a portion of the pusher.). Of course, base 11 may be any other configuration depending on the desired result such as square or shaped to interconnect with a wrench or other suitable tool.

In the present embodiment, three retractor blades 12 are spaced circumferentially around base 11. Each blade 12 includes extended portion 12a and hinge portion 12b, wherein each blade 12 is hinged by a respective hinge-pin 13 (located in hinge portion 12b, to base 11. One skilled in the art, however, will understand that any number of blades 12 may be employed. In one embodiment, blades 12 are spring-biased toward a closed position, as shown, by springs 19. Each blade has its own spring 19 associated with its respective hinge pin, and discussed in further detail below. Although the use of independent coil springs are shown in the respective figures, one skilled in the art will readily understand that alternative spring means may be employed. For example, elastic membranes or materials (rubber for example) may be used in place of the springs. In one embodiment, an elastic washer (e.g., an O-ring) is circumferentially disposed, encircling areas between base 11 and hinge portion 12b of all three hinge portions 12. Thus, when any of the blades is moved into an open or retracted position, the washer provides elastic force in response thereby biasing the blades 12 toward their closed position. The use of a singular O-ring may have advantages in manufacturing costs or assembly. In another alternative embodiment, the blades 12 may be molded together with base 11 with a plastic material where the blades are biased inward based on the elasticity of the plastic material used.

Pusher mechanism 14 is threadably engaged to base 11 for movement in and out thereof. The Pusher mechanism 14 is manually rotatable by grasping by a user (e.g., a surgeon, aid, or device) and turning knob finger tabs 15. In an alternative embodiment, the dilator mechanism (including knob 16) may be welded to pusher mechanism 15. Operation of the entire retractor device including the pusher mechanism shall be discussed below.

Dilator mechanism knurled knob 16 (hereinafter knob 16) is threadably engaged with pusher mechanism 15, similar to the thread-able engagement between pusher 15 and base 11, and is shown in FIG. 1 in its tightened-down position (completely inserted into pusher mechanism 15). Pusher mechanism threads 190, with which dilator mechanism thread-ably engages, are shown in perspective FIG. 19. Dilator mechanism knurled knob 16 may be welded, adhered or attached by any other means as well. Dilator mechanism tip 16t, at the left hand side of FIG. 1, is open at its center (to ride over the guide-wire) and is connected to knob 16 by a hollow dilator tube 42 (See FIG. 4 and FIG. 21). The dilator tube 42 and tip 16t form a completely open interior to accommodate insertion of a guide-wire (not shown) therethrough. Finger tab 17 is fixedly connected to base 11 to provide a protuberance for firm grasping by the user or other individual using the device. In one embodiment, the finger tab 17 is located at a position on the base 11 in alignment with one of the three blades which is longer than the other two blades (not shown in FIG. 1). By noting location of tab 17, the user knows the location of the longer blade. The significance and functionality of this longer blade length variation is discussed below. It will be understood, however, that the blades 12 may be all the same length, varying lengths or any combination therebetween and the present description should not be construed as limiting. In another embodiment, finger tab 17 may be located at a specific radial position (164 degrees from some reference point for example) to aid in a specific surgical procedure. It will be understood that finger tab 17 may be located at any radial position suitable for its desired purpose.

FIG. 2 is an end view of retractor device 10 shown in FIG. 1. In this FIG. three finger-tabs 15, 15a and 15b are shown spaced evenly around and extending from dilator knob 16. Also shown is finger-tab 17 which is fixedly connected to base 11. In operation, after a stab incision is made by the user and after a guide-wire is inserted into the stab incision to determine appropriate penetration depth, location or other desired use of the guide-wire, hollow tip 16t (FIG. 1) is inserted over the guide-wire and pushed into the body of the patient. To accomplish this penetration, the user or other individual using the device may use any of the finger-tabs 15, finger tab 17 and/or knob 16 to provide a good structure for grasping. One will understand that grasping may be done by either human or mechanical means (for example wrench or robotic device). In one embodiment, a rotary motion, clockwise and counter-clockwise of the entire retractor device 10, and other motions can thus be used to work the retractor device 10 into the patient and into its needed position to position tip 16t at the optimum location in the operative field. The guide-wire (not shown) protrudes from aperture 20 and can be withdrawn through aperture 20 when the optimum location is obtained, or before or after that occurrence or with the removal of the dilator itself. During this portion of the operation, blades 12 are in the closed position as shown in FIG. 1. The tip 16t may also be used to auto-position the device at the desired location. When used in spinal disc surgery, the tip 16t may be auto-located inside the disc at the desired location such that when the dilator assembly 14, 15, 16 is removed, the blades 12 are in the correct position to be opened at the desired location. In one embodiment, this is accomplished through positioning the tip 16t between vertebras.

FIG. 3 is a perspective view of the embodiment of FIG. 1. Blade $12_L$ is the longer blade noted above and, as depicted, it aligns with finger tab 17 affixed to base 11 (although it may be at any radial position). Longer blade $12_L$ may be considered a multipurpose blade for use during a procedure generally providing for retraction of specific anatomy, identification/targeting specific anatomy, sweeping an area to move away anatomy, and identification of the device within the patient (e.g., under various imaging modalities), as discussed herein.

FIG. 4 is a cross-sectional view of the embodiment of FIG. 1, taken along the section 4-4. The hinge pin 13 depicted as a black dot is shown axially and is the hinge pin associated with longer blade $12_L$ and about which blade $12_L$ rotates. Spring 19 is shown seated in a recessed portion of base 11 and presses against shoulder 40 of blade $12_L$, wherefore spring 19 is biased in a manner to keep blade $12_L$ closed, as shown (such may be the same for remaining blades 12). As discussed above, other biasing means may be used instead of spring 19 shown herein. Pusher tube (or expander tube) 41 extends from pusher 14 to a distal location between the blades 12. Pusher tube 41 has a distal end 41a that is set in length from pusher 14 such that when pusher mechanism 14 is fully tightened into and bottomed out in base 11, distal end 41a will either be positioned at or above section 51 of any of the blades 12 or between section 51 for reasons that will be discussed and depending on the desired operation. In the embodiment shown in FIGS. 1 and 4, distal end 41a is positioned at or above section 51 such that in its tightened position, distal end 41a does not abut section 51 and therefore the blades 12 are not expanded. In this configuration, the retractor device 10 is positioned into a patient while the blades 12 are in their contracted position.

FIG. 5 is a top plan view of the embodiment of FIG. 1 according to another embodiment. In this embodiment, the pusher assembly (collectively pusher 14, pusher tube 41, dilator tube 42 and knob 16) is replaced with a second pusher assembly 15. Alternatively, instead of the entire pusher mechanism, the dilator including its knob 16, tube 42 and tip 16t may be removed leaving the remaining items of the pusher assembly. Blades 12 are still in a closed position. Blades 12 each have three sections 50, 51 and 52, shown in FIG. 5. Section 50 extends substantially uniform in diameter such that pusher tube 41 is positioned along the interior in a non-interfering way between blades 12. Section 51 has a tapered configuration to abut against distal end 41a as will be discussed. Section 52 forms an extended tapered configuration with blades 12 as needed for working the device 10 into the operative area. The relationship between cylindrical configuration 50 and conic configuration 51, both configurations formed by the three blades while in a closed position, is responsible for spreading the blades, and is discussed in detail below. However, one skilled in the art will understand that the tube 42 may interact with blades 12 through any other means known in the art to expand the blades 12. For example, tube 12 could include gear teeth that mate with teeth on blades 12 to cause gear like rotation of blades 12 about the hinge.

FIG. 6 is an end view of the configuration of FIG. 5. Two blades 12 and one blade $12_L$ are visible in the center of the Figure. Light posts 60 are attachments for light fibers or light cables (not shown) used for illuminating the surgical site. The light posts also serve as detents for control of surgical instruments (not shown in this FIG.) used with the configuration of FIG. 5, to be discussed below. FIG. 7 is the same perspective view as that presented in FIG. 3, but with the dilator removed.

FIG. 8 is a cross-sectional view of the embodiment of FIG. 5 taken along the section 8-8. Pusher tube 41 is shown to have a length which, while the pusher 14 is in a relatively unthreaded and non-bottomed out position, does not enter section 51 of the blades. As such, springs 13 maintain sufficient force onto shoulders 40 to hold blades 12 and $12_L$ in closed positions as shown. The structure through which hinge pin 13 is inserted has hard edge 80 which serves as a limit stop to the advancement of pusher 14 as it is threaded into base 11, operation of which is discussed below.

With reference to FIGS. 8 and 12, the operation of the embodiment is described. In FIG. 8, the pusher 14 is in its unthreaded state. Next, pusher 14 is threaded into base 11 such that distal end 41 engages section 51. As can be seen in FIG. 12, distal end 41a abuts section 51 and expands blades 12 apart and against the biasing of springs 19. The pressure against section 51 by distal end 41a and the counter force by springs 19 create a degree of rigidity that holds blades 12 in place. Of course, one will understand that springs are not necessary and only distal end 41a against section 51 may be employed. The angle of section 51 may be chosen such that an optimum force or speed of retraction may be achieved. For example, the angle of section 51 may be chosen shallow such that more rotation of pusher 14 is required for each degree of opening for blades 12. This will provide a relatively larger amount of torque where opening the operative area is difficult and needs more force. Likewise, where speed is desired, the angle of section 51 may be steeper such that a greater degree of opening will be achieved with each rotation of pusher 14. Additionally, the sections 51 of each blade 12 may be pitched differently to cause blades 12 to open at different rates per rotation of pusher 14.

FIG. 9 is a top plan view of the embodiment of FIG. 5 after the blades have been outwardly displaced or spread apart. At the left-hand side of the drawing, it can be readily seen that the end of blade $12_L$ extends beyond the ends of blades 12 and that all blades are spread apart. In FIG. 9, it can be seen that pusher 14 has been screwed or threaded into base 11 to the maximum extent possible. It will be noted that the depth of pusher threaded into base 11 or the degree of stop between shoulder 40 against base 11 may be set to ensure the blades 12 open only a predetermined amount.

FIG. 10 is an end view of the configuration of FIG. 9, being the same end view as that of FIG. 6 but with the blades in their open and expanded configuration. Two blades 12 and one blade 12$_L$ are shown, Open space 61 is provided between the blades in FIG. 10 representing vision into the operative area that allows the user or the user to access the targeted for surgical intervention. Tabs 15 are shown in the same position in which they appeared in FIG. 6. For ease of presentation; however, it should be understood that after pusher 14 has been screwed into base 11 to the desired distance to achieve the desired expansion of the blades 12, as shown, there is no requirement that tabs 15 on the pusher maintain the same relative position with respect to tab 17 on the base 11, although that may coincidentally occur. FIG. 11 is the same perspective view as that presented in FIG. 7, but with the blades outwardly displaced, shown at end 110 of blades 12 and 12$_L$.

FIG. 12 is a cross-sectional view of the embodiment of FIG. 9, the view taken along the section 12-12. Pusher 14 is shown as coincidentally being completely threaded into base 11 while structure of base 11 simultaneously abuts limit stop edge 80. However, in one embodiment, limit stop 80 is the primary mechanism to prevent further movement of pusher tube 41 and corresponding expansion of the blades 12. Further, in another embodiment, the limit stop 80 is positioned such that it is reached before spring 19 is fully compressed to ensure that no excessive wear or damage results to spring 19. It should be noted that pusher tube 41 has necessarily advanced to the left in FIG. 12 and, by that translational motion, it is pressing against the inside walls of section 51 of the blades. This motion against section 51 causes the blades to spread apart, against counterforce spring resistance from springs 19 as shown by the contact between blade-shoulder 40 and spring 19. The ends of the blades 110 are shown spread apart. The spreading of the blades is constrained to an outward displacement limit as determined by the transverse movement limit of pusher tube 41 which, in turn, is determined by limit stop 80. In an alternative embodiment, in the structure containing hinge pin 13 (FIG. 8), the face of that structure opposite to that of limit stop 80 can be extended to the left to further reduce motion of shoulder 40 and, if extended sufficiently can be an alternative limit stop to that provided by face 80.

Different retractors can be designed for different surgical tasks. Different retractors can have different outward blade displacement limits as functions of different pusher tube lengths and/or as functions of different degrees of taper of section 51. Typically, these displacements may be in the two (2) to twelve (12) millimeter range, but is not limited to any particular displacement amount. The more severe the taper of section 51, the greater the blade displacement is obtained per angle of rotation of pusher tabs 15. With other parameters being equal, however, a greater taper to section 51 yields a greater effort than otherwise is required by the user in rotating pusher tabs 15 to achieve that greater blade displacement. Conversely, the less severe the taper of section 51, the smaller the blade displacement is obtained per angle of rotation of pusher tabs 15 with other parameters being equal. However, with a lesser taper to section 51, a lesser effort than otherwise is required by the user in rotating pusher tabs 15 to achieve that lesser blade displacement. Different retractors having these different mechanical advantages requiring greater or lesser effort are advantageously used in different surgical scenarios. Moreover, the opening distance between blades 12 may be adjustable for various procedures. The adjustment may be predetermined based on the dimensions of the components, or it may be adjustable during a procedure by utilizing pusher tubes 41 of various lengths. In an example, a larger opening retractor device may be used by OB/GYN procedures. Examples of opening distances may include two millimeters (2 mm) to eighteen millimeters (18 mm), or more. The opening distances (see ends 110 of FIGS. 11 and 12) of the blades 12, and the associated size of all components, may be smaller or larger for any given procedure and are not limited by the exemplary embodiments described herein.

FIG. 13 is a top plan view of the exemplary embodiment of FIG. 9, but after a surgical tool is inserted into the embodiment. Surgical tool 130 is threadably and concentrically connected to pusher 14 similarly to how dilator knob 16 was threadably and concentrically connected to pusher 14. Surgical tool 130 is intended to represent a generic tool, and its end 131 protrudes beyond the ends 110 of blades 12 and 12$_L$. The device 10 can be a conduit used, for example, to allow illumination and viewing if operatively connected to fiber optic light sources (via light terminals 60 in FIG. 14). Or, device 10 can be used to allow a different device to perform suction, or it could be used to allow other instrumentation to occupy the conduit to function as a clipper, a caliper, a pincher, a cauterizer, etc., depending on what is threadably attached to pusher 14 and what is inserted into the conduit.

FIG. 14 is an end view of the configuration of FIG. 13, being the same end view as that of FIG. 10, but with the surgical tool in place. Surgical tool 130, regardless of its utility or function, can be configured with a plurality of handle-indentations 131 to serve as both convenient handgrips and detents relative to light posts 60. In other words, light posts 60, which supply fiber optic light paths to the surgical sight, also serve as posts which can provide mechanical detents to hold surgical tool 130 in place, after the user positions it to his/her liking. FIG. 15 is the same perspective view as that presented in FIG. 11, but with surgical tool 130 in place, its end 131 showing beyond the ends 110 of the blades. FIG. 16 is a cross-sectional view of the embodiment of FIG. 13, taken along the section 16-16, with tool 130 in place.

FIG. 17 is another perspective view of tissue retractor device 10 in a closed-blade state with it including pusher 14 but not dilator 16 as shown in FIG. 1. Tool 130 cannot be included within the device in this view, because the device is in a closed-blade state. Longer blade 12$_L$ is clearly visible in this view and is aligned with tab 17 on the base.

FIG. 18 is an exploded view of the embodiment of FIG. 17, but axially rotated therefrom to more clearly show certain detailed mechanical features of the embodiment. Each bladeshoulder 40 is held in place by hinge pin 13 when inserted into apertures 13a. As can be seen from the FIG., each spring 19 pushes against its respective shoulder 40 from the side opposite to the side seen in the FIG., and because of the location of hinge pin 13 and its apertures 13a relative to the point of force from spring 19 onto the shoulder, each blade 12 is pressed against the other two blades which are similarly biased. In other words, all three blades are pressed against each other as a result of the three springs pushing, respectively, against the three shoulders. The interior surfaces, or a portion of an interior surface, of blades 12, 12$_L$ may be finished to provide reduced glare from illumination or to provide improved illumination conditions. The color of the interior surface may also be selected to provide improved illumination depending on the procedure. Examples of finishes may include a flat finish, a mirrored finish, and/or a colored finish.

Figure 20:
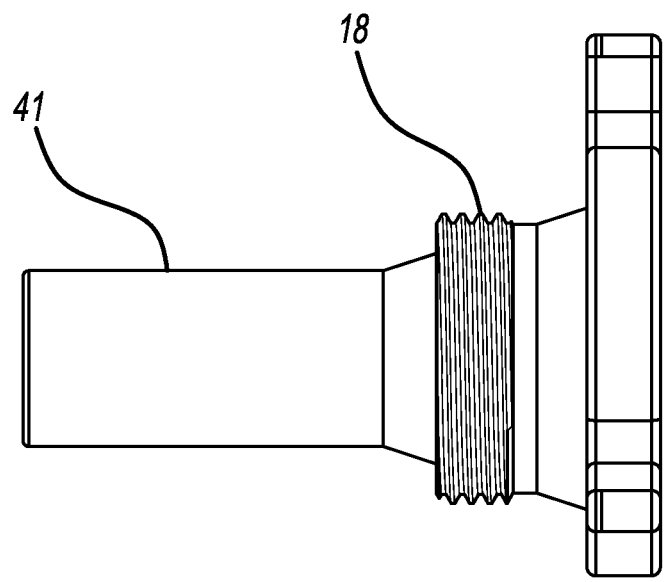
FIG. 20 is a side view of the pusher mechanism depicted in FIG. 19.

FIG. 19 is a perspective view of the pusher mechanism shown in cross section in FIGS. 4, 8, 12 and 16. Threads 190 are shown which are arranged to receive, concentrically, first the dilator 16 and, after that fulfills its purpose and is removed (unscrewed), then surgical tool 130. FIG. 20 is a side view of the pusher mechanism depicted in FIG. 19. Pusher tube or expander tube 41 is cylindrical in shape, and readily fits within the generally cylindrical shape 50 formed by the three blades. However, the diameter of cylindrical pusher tube 41 is larger than radially-taken cross sectional diameters of the three blades providing conical shape 51. Therefore, the blades are forced open against opposing bias forces of springs 19 when the pusher handle tabs 15 are rotated because that causes pusher tube 41 to acquire translational motion and advance towards blade ends 110, thereby spreading those blades to allow that translational motion.

Figure 21:
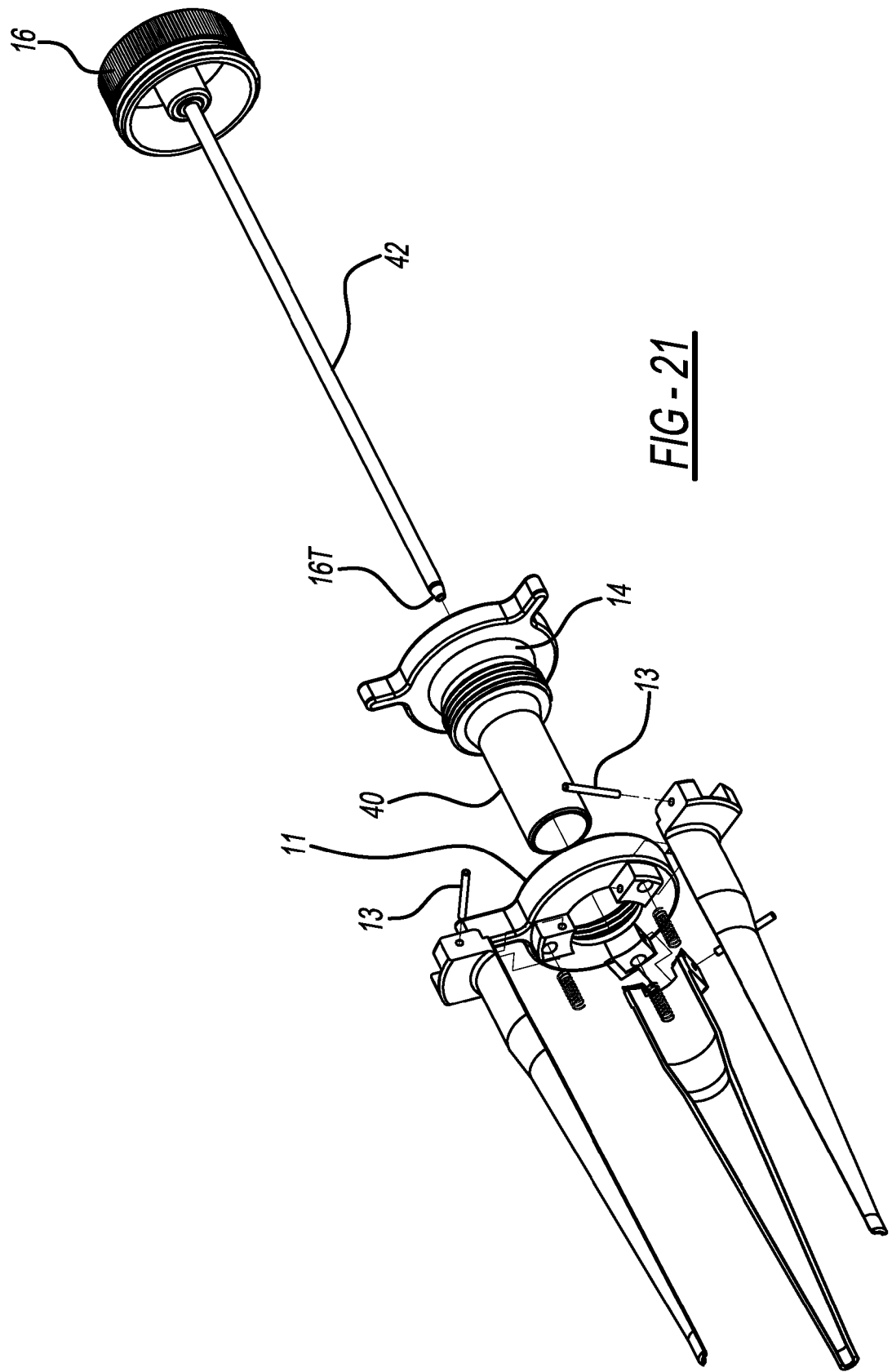
FIG. 21 is an exploded view similar to that of FIG. 18, but also showing the dilator depicted in cross section in FIG. 4.

FIG. 21 is an exploded view similar that of FIG. 18, but also showing the dilator depicted in cross section in FIG. 4. Knob 16 is shown, along with dilator tube 42 and dilator tip 16*t*. Knob 16 screws into pusher mechanism 14 which, in turn, screws into base 11.

Figure 22:
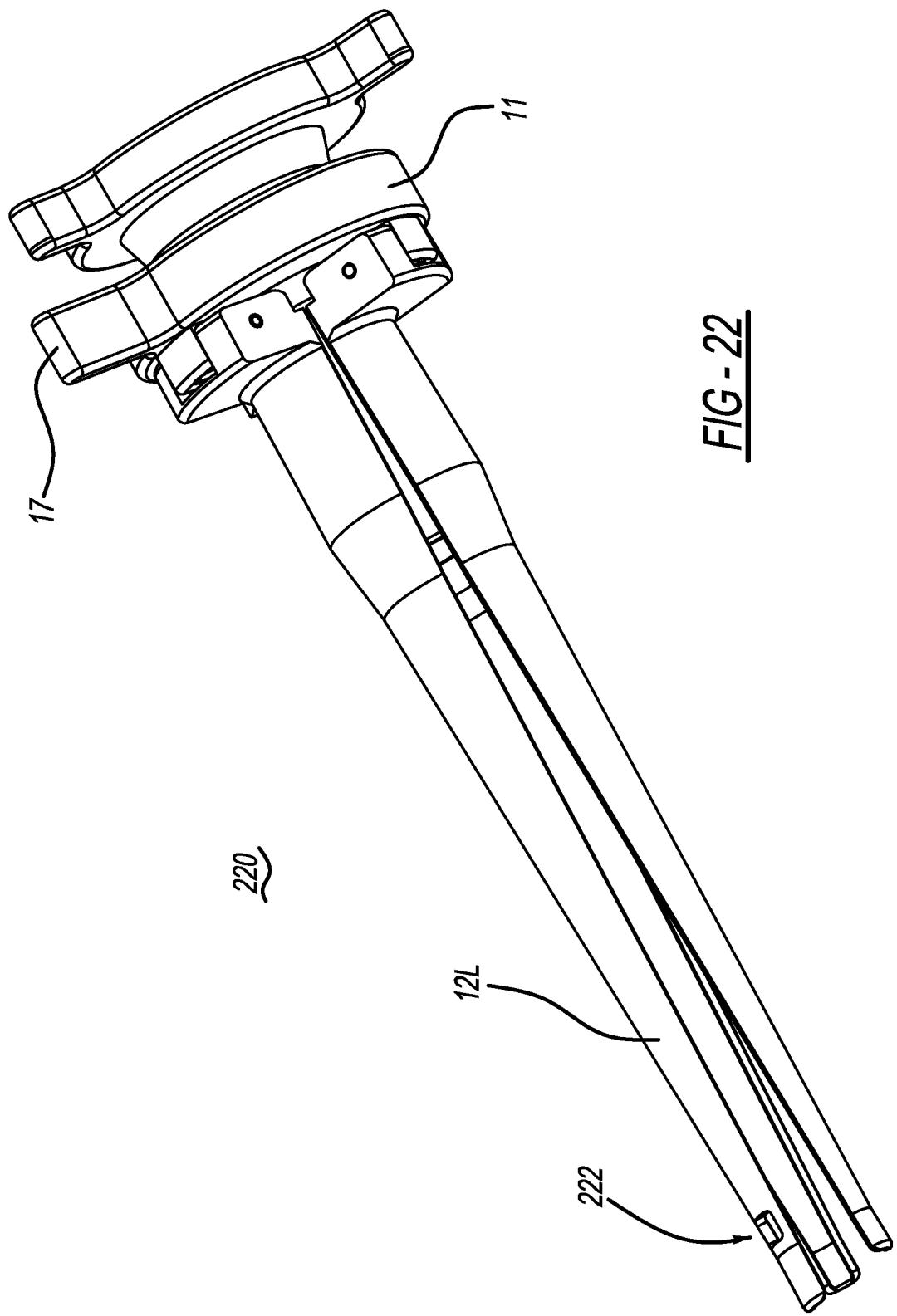
FIG. 22 is a perspective view of an alternative embodiment of the retractor device.

FIG. 22 is a perspective view of an alternative embodiment 220 of the retractor device. Additional features may include a window 222 through blade 12$_L$ where a user may access tissue from the side for sampling. The windows may be located, for example, to allow access by biopsy devices placed through pusher tube 41. The windows may also be configured to allow tissue to protrude through one or more of blades 12 such that inspection and/or sampling of the tissue may be performed (biopsies for example). As shown, window 222 is aligned with the blade 12$_L$ that is also aligned with finger tab 17 that provides the position to the user. Additionally, blades 12 may include a number of windows (e.g., openings therethrough) to provide additional opportunities for tissue inspection, resection, reduce weight and/or alter structural rigidity and strength. Moreover, blades 12 may be partially or substantially skeletonized.

In operation of the above-described embodiment, referring to all Figures collectively, the user first makes a stab incision and may insert a guide-wire to determine depth of penetration. Then, if a guide-wire is used, the user inserts the device 10 in FIG. 1, including the dilator mechanism having knob 16, over the guide-wire which enters the dilator mechanism via the hole in tip 16*t*. The user grasps base 11 including tab 17 with one hand and grasps pusher/pusher tabs/knob combination 14/15/16 with the other hand and, without rotating pusher 14 relative to base 11, slides device 10 down the guide-wire and works device 10 into the body of the patient by clockwise and counterclockwise and other motion. These tabs offer a secure gripping configuration for the user. All blades 12 and 12$_L$ remain closed during this portion of the procedure by force of springs 19. If no guide-wire is used, the same procedure may be followed without interacting with the guide-wire. After tip 16*t* is positioned in the correct position, and this can be determined by any known means in the art including fluoroscopy or other means in combination with a radio opaque tip 16*t* or a radio opaque end of blade 12$_L$, dilator assembly and the guide-wire can be removed. Alternatively, the retractor may be auto-located with or without the use of imaging as discussed herein.

Then, with the blades remaining closed, the user, in one embodiment, uses longer blade 12$_L$ to maneuver around nerve roots and/or other structure(s) in his/her path (this may be done before or after removal of the guide wire), without damaging nerves or causing an unwanted result. The longer blade 12$_L$ is advantageous for this purpose because it offers a small effective tip at the end of device 10 as compared with an embodiment having same-length legs 12 (e.g., substantially equal length legs). This smaller tip permits easier maneuvering around nerve root obstructions and the like which, importantly, supports better patient outcomes. Other embodiments may include retractor devices having two or more blades. In practice, the longer blade 12$_L$ may be used to sweep an area such that the user to move aside specific anatomy (e.g., an exiting nerve root). The sweep procedure may be performed by turning the retractor. Additionally, the longer blade 12$_L$ may be used to retract or specify certain anatomy or to provide improved targeting during imaging using a radio opaque material near the distal end. An example of specifying particular anatomy, the longer blade 12$_L$ may be used to target an exiting nerve root and controllably retract/push it aside.

Next, the user installs the dilator assembly shown in FIG. 8 that includes a longer pusher tube 41. The user rotates tabs 15 relative to tab 17 to advance pusher tube 41 into the vicinity of section 51. The rotational motion of tabs 15 and, thus, rotational motion of threads 18, provide translational motion to pusher tube 41 which, in turn, presses against section 51, thereby spreading blades 12 and 12$_L$ against force of springs 19. The spreading of these blades pushes patient tissue out of the way so the user can have clear access to the site 61 as shown in FIG. 10, such as vertebrae or discs, upon which surgical procedures shall be performed. Surgical tools and/or instrumentation are introduced through the opening to site 61 which can be held in place by detents in combination with light terminals 60.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A tissue retractor device for retracting tissue, said device comprising:
   a base connected to a plurality of rigid blades distributed around said base, each of said blades being outwardly rotatable from the base, wherein one of said blades is a longer blade than the other of said blades, wherein a remainder of said blades are of substantially a same length such that the longer blade extends beyond the remainder of said blades for retracting tissue during an operating procedure; and
   a pusher engaged to said base, said pusher movable in a longitudinal direction to move said blades to angularly displace each of said blades from a respective closed position to an open position;
   wherein the plurality of blades comprises three blades;
   wherein the longer blade further comprises:
      a non-tapered portion adjacent the base;
      a tapered region extending from the non-tapered portion to a tip of said longer blade; and
      a substantially uniform region located at the tip, wherein the uniform region has an outer face that is substantially parallel to a longitudinal axis of the tissue retractor device and a substantially uniform width in a direction across the outer face;
   wherein the uniform region extends from a location before an end of the remainder of the plurality of blades to a point beyond the location of the end of said remainder of the plurality of blades.

2. The device of claim 1, wherein the pusher threadably engages said base such that rotation of the pusher moves the pusher in said longitudinal direction.

3. The device of claim 2, wherein:
   the pusher further comprises a pusher tube;
   each of the blades includes a sloped portion that abuts the pusher tube; and
   longitudinal movement of the pusher pushes the pusher tube against the sloped portions to expand the blades.

4. The device of claim 3, further comprising at least one elastic device positioned between a portion of the blades and the base to bias the blades toward a closed position.

5. The device of claim 4, wherein the elastic portion is a plurality of springs, wherein each of the springs biases a respective one of the plurality of blades.

6. The device according to claim 1 wherein:
   said pusher further comprises at least one radially-protruding grasping tab; and
   said base further comprises a radially-protruding locater tab, wherein said locater tab is disposed on said base such that said locater tab aligns longitudinally with said longer blade.

7. The device according to claim 3, wherein the slope of the blades are configured to maximize torque in opening the blades.

8. The device according to claim 3, wherein the slope of the blades is configured to maximize speed in opening the blades.

9. The device according to claim 1, further comprising at least one light guide disposed in said base and adapted to provide optical illumination.

10. The device according to claim 9, wherein an interior portion of the blades is reflective to provide better illumination.

11. The device according to claim 9, wherein an interior portion of the blades is a flat finish to provide reduced glare from illumination.

12. The device according to claim 9, wherein an interior portion of the blades is a colored finish.

* * * * *